(12) United States Patent
Melsheimer (10) Patent No.: US 9,125,765 B2
(45) Date of Patent: Sep. 8, 2015

(54) IMPLANT DEPLOYMENT RESTRAINT DEVICE

(75) Inventor: Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 903 days.

(21) Appl. No.: 13/323,048

(22) Filed: Dec. 12, 2011

(65) Prior Publication Data

US 2012/0150272 A1 Jun. 14, 2012

Related U.S. Application Data

(60) Provisional application No. 61/422,425, filed on Dec. 13, 2010.

(51) Int. Cl.
*A61F 2/06* (2013.01)
*A61F 2/966* (2013.01)

(52) U.S. Cl.
CPC ......... *A61F 2/966* (2013.01); *A61F 2002/9665* (2013.01); *Y10T 29/49908* (2015.01)

(58) Field of Classification Search
CPC ... A61F 2002/9665; A61F 2/95; A61F 2/962; A61F 2/966
USPC ....................................................... 623/1.11
See application file for complete search history.

(56) References Cited

U.S. PATENT DOCUMENTS

| | | | |
|---|---|---|---|
| 4,768,507 A | 9/1988 | Fischell et al. | |
| 5,702,418 A | 12/1997 | Ravenscroft | |
| 5,733,325 A | 3/1998 | Robinson et al. | |
| 6,077,295 A | 6/2000 | Limon et al. | |
| 6,258,099 B1 * | 7/2001 | Mareiro et al. | 606/108 |
| 6,395,017 B1 | 5/2002 | Dwyer et al. | |
| 6,520,983 B1 | 2/2003 | Colgan et al. | |
| 6,607,551 B1 | 8/2003 | Sullivan et al. | |
| 7,264,632 B2 | 9/2007 | Wright et al. | |
| 7,473,271 B2 | 1/2009 | Gunderson | |
| 2004/0204749 A1 * | 10/2004 | Gunderson | 623/1.12 |
| 2006/0206187 A1 | 9/2006 | Parker et al. | |
| 2007/0208405 A1 | 9/2007 | Goodin et al. | |
| 2009/0048653 A1 | 2/2009 | Jordan et al. | |
| 2009/0276027 A1 | 11/2009 | Glynn | |
| 2009/0287290 A1 | 11/2009 | Macaulay et al. | |

FOREIGN PATENT DOCUMENTS

EP 0 834 293 A1 10/1997

* cited by examiner

*Primary Examiner* — Gregory Anderson
(74) *Attorney, Agent, or Firm* — Brinks Gilson & Lione (57) ABSTRACT

A restraint member is provided for preventing longitudinal movement between a self-expanding medical implant and the inner catheter upon which the implant is mounted. The restraint member may be particularly useful for a woven wire self-expanding stent where the restraint member is positioned only under one or more ends of the stent.

22 Claims, 8 Drawing Sheets

IMPLANT DEPLOYMENT RESTRAINT DEVICE

This application claims priority to U.S. Provisional Application No. 61/422,425, filed Dec. 13, 2010, which is hereby incorporated by reference herein.

BACKGROUND

The present invention relates generally to medical devices and more particularly to a delivery system for a self-expanding implant.

Self-expanding implants are used for numerous medical procedures. For example, a particularly useful type of self-expanding implant is a stent. Stents are commonly used to expand and maintain patency of a vessel suffering from stenosis, and may be used to treat numerous arteries throughout the vasculature. In addition, stents may be used in combination with graft layers to treat aneurysms in the vasculature. Other types of self-expanding implants include filters, valves, etc.

Self-expanding medical implants are typically deployed within a body with a minimally invasive delivery system. Typically, the delivery system has an inner catheter that extends from a proximal handle, which remains outside the patient's body during the deployment procedure, and the distal end of the delivery system, which passes through the patient's body to the treatment site. The self-expanding implant is compressed onto the inner catheter to present a small diameter to ease travel of the delivery system through the patient's body. An outer sheath is positioned over the self-expanding implant and inner catheter to retain the self-expanding implant in the compressed state prior to deployment.

When the delivery system is positioned at the intended treatment site, the physician typically actuates the proximal handle so that the outer sheath is withdrawn from the self-expanding implant and inner catheter. This allows the self-expanding implant to expand outward toward the vessel wall and away from the inner catheter. The inner catheter and outer sheath may then be withdrawn from the patient's body, and the implant may be left at the treatment site.

One problem with conventional delivery systems for self-expanding implants is that it can be difficult to maintain precise control over the implant during the deployment procedure. For example, during deployment self-expanding implants sometimes spontaneously deploy from the delivery system when the outer sheath is only partially withdrawn from the implant. This can occur because the outer sheath is often made from a lubricious material to reduce friction between the self-expanding implant and the outer sheath during withdrawal of the outer sheath. This is an important feature of delivery systems for self-expanding implants because the friction between the implant and the outer sheath can be so high that it can be difficult for the physician to apply enough force to withdraw the outer sheath. However, once the outer sheath has been withdrawn enough to expose the distal end of the implant, the self-expanding implant begins to expand away from the inner catheter. The longitudinal force caused by the distal end of the implant expanding can be enough to pull an additional portion of the implant out of the outer sheath. This can be a particular problem when lubricious materials are used for the outer sheath since the frictional force between the implant and outer sheath is reduced. This can result in imprecise placement of the implant since it can be challenging to predict exactly how the implant will expand during deployment.

In some situations, it may also be desirable to retain a solid connection between the inner catheter and the implant until the outer sheath has been fully withdrawn from the implant. This may be useful if the physician may want to move the implant to a different location after partially deploying the implant. A physician may also want to fully compress a partially deployed implant in order to remove the implant from the patient's body without fully deploying the implant. However, these options are difficult with conventional delivery systems. For example, once a self-expanding implant is partially deployed with a conventional delivery system, the distal end of the implant typically comes into contact with the vessel wall of the patient. When this occurs, friction results between the implant and the vessel wall. If a physician attempts to remove the delivery system in this situation, the friction between the distal end of the implant and the vessel wall will typically pull the remaining portion of the implant out of the outer sheath. In addition, if a physician attempts to push the outer sheath back over a partially deployed implant, the contact between the distal end of the outer sheath and the implant will typically push on the implant and cause the implant to slide distally relative to the inner catheter.

Accordingly, the inventor believes it would be desirable to provide a new delivery system for self-expanding implants with a deployment restraint member.

SUMMARY

A restraint member is described with a hub and protrusions extending from the outer surface of the hub. The protrusions extend through openings in a self-expanding medical implant to provide a solid connection between the inner catheter and the implant. Preferably, the restraint member is located only at the ends of the implant so that the middle portion of the implant is directly mounted onto the inner catheter.

The invention may include any of the following aspects in various combinations and may also include any other aspect described below in the written description or in the attached drawings.

A medical device, comprising:
an inner catheter comprising an outer diameter along a distal portion of the inner catheter;
a restraint member disposed on the inner catheter, the restraint member comprising an inner diameter, a hub extending from the inner diameter and around the restraint member, and a plurality of protrusions extending outward from an outer surface of the hub, each of the protrusions comprising a base at the outer surface of the hub and an outer end, the base being larger than the outer end, wherein the restraint member comprises a row of the protrusions around a circumference of the hub, the inner diameter of the restraint member being bonded to the inner catheter along the distal portion of the inner catheter;
a self-expanding stent compressed onto the inner catheter and the restraint member, the self-expanding stent comprising elastic wire with a plurality of bends at a proximal end and a distal end of the stent, the wire being woven between the proximal and distal ends, wherein each of the protrusions extends through an opening formed by one of the bends at the proximal end of the stent, the hub thereby being disposed under the proximal end of the stent and no other protrusions on the restraint member extending through an opening of the stent, a middle portion of the stent being disposed on the outer diameter of the inner catheter, wherein the outer diameter of the inner catheter is smaller than the outer surface of the hub of the restraint member; and an outer sheath disposed over the inner catheter, the restraint member, and the stent.

The medical device wherein the protrusions are oblong-shaped.

The medical device wherein the protrusions fill about 80% to about 90% of the open area of each of the openings, the open areas being defined by the bends and adjacent struts of the stent when the stent is compressed.

The medical device wherein the protrusions are tapered from the base to the outer end about 10° to about 20°.

The medical device wherein the protrusions are cone-shaped.

The medical device wherein the protrusions are pyramid-shaped.

The medical device wherein the restraint member is made from a polymer.

The medical device further comprising a stop surface disposed proximally adjacent the hub of the restraint member, the stop surface extending outward from the outer surface of the hub.

The medical device further comprising a second restraint member disposed at the distal end of the stent, wherein each of the protrusions of the second restraint member extends through an opening formed by one of the bends at the distal end of the stent, the hub of the second restraint member thereby being disposed under the distal end of the stent and no other protrusions on the second restraint member extending through an opening of the stent.

The medical device wherein an open space is disposed between the bends of the proximal end and the distal end of the stent and the stent and the outer diameter of the inner catheter, no portion of the outer diameter of the inner catheter extending outward from the outer surface of the restraint member between the bends of the proximal end and the distal end of the stent.

The medical device wherein an open space is disposed between the bends of the proximal end and the distal end of the stent and the stent and the outer diameter of the inner catheter, no portion of the outer diameter of the inner catheter extending outward from the inner diameter of the restraint member between the bends of the proximal end and the distal end of the stent.

The medical device wherein the restraint member is made from a polymer, further comprising a stop surface disposed proximally adjacent the hub of the restraint member, the stop surface extending outward from the outer surface of the hub, and wherein an open space is disposed between the bends of the proximal end and the distal end of the stent and the stent and the outer diameter of the inner catheter, no portion of the outer diameter of the inner catheter extending outward from the outer surface of the restraint member between the bends of the proximal end and the distal end of the stent.

The medical device wherein no portion of the outer diameter of the inner catheter extends outward from the inner diameter of the restraint member between the bends of the proximal end and the distal end of the stent.

The medical device further comprising a second restraint member disposed at the distal end of the stent, wherein each of the protrusions of the second restraint member extends through an opening formed by one of the bends at the distal end of the stent, the hub of the second restraint member thereby being disposed under the distal end of the stent and no other protrusions on the second restraint member extending through an opening of the stent.

The medical device wherein the protrusions of the restraint member and the second restraint member are pyramid-shaped.

The medical device wherein the protrusions are oblong-shaped, the protrusions fill about 80% to about 90% of the open area of each of the openings, the open areas being defined by the bends and adjacent struts of the stent when the stent is compressed, and the protrusions are tapered from the base to the outer end about 10° to about 20°

The medical device further comprising a stop surface disposed proximally adjacent the hub of the restraint member, the stop surface extending outward from the outer surface of the hub, and wherein an open space is disposed between the bends of the proximal end and the distal end of the stent and the stent and the outer diameter of the inner catheter, no portion of the outer diameter of the inner catheter extending outward from the inner diameter of the restraint member between the bends of the proximal end and the distal end of the stent.

The medical device wherein the protrusions are oblong-shaped.

The medical device wherein the protrusions fill about 80% to about 90% of the open area of each of the openings, the open areas being defined by the bends and adjacent struts of the stent when the stent is compressed, and the protrusions are tapered from the base to the outer end about 10° to about 20°

The medical device wherein the protrusions are cone-shaped.

A method of manufacturing a medical device, comprising:
providing an inner catheter comprising an outer diameter along a distal portion of the inner catheter;
providing a tube comprising an inner diameter;
forming a plurality of protrusions on the tube, wherein after forming the protrusions the tube comprises an outer surface with the protrusions extending outward therefrom and a thickness between the inner diameter and the outer surface;
sliding the inner diameter of the tube over a distal end and the outer diameter of the inner catheter;
bonding the inner diameter of the tube to the inner catheter;
compressing a self-expanding stent onto the inner catheter and the tube, wherein the stent comprises elastic wire with a plurality of bends at a proximal end and a distal end of the stent, the wire being woven between the proximal and distal ends, wherein each of the protrusions extends through an opening formed by one of the bends at the proximal end of the stent, the tube thereby being disposed under the proximal end of the stent and no other protrusions on the tube extending through an opening of the stent, a middle portion of the stent being disposed on the outer diameter of the inner catheter, wherein the outer diameter of the inner catheter is smaller than the outer surface of the tube;
sliding an outer sheath over the compressed stent, the inner catheter and the tube.

The method further comprising bonding a distal tip onto the distal end of the inner catheter after sliding the tube over the distal end and before the stent is compressed onto the inner catheter.

The method further comprising:
sliding an inner diameter of another of the tube over the distal end and the outer diameter of the inner catheter;
bonding the inner diameter of the another of the tube to the inner catheter; and wherein each of the protrusions of the another of the tube extends through an opening formed by one of the bends at the distal end of the stent, the another of the tube thereby being disposed under the distal end of the stent and no other protrusions on the another of the tube extending through an opening of the stent.

The method wherein the forming the plurality of protrusions on the tube comprises building the protrusions up from the tube.

The method wherein the forming the plurality of protrusions on the tube comprises removing material from the tube.

The method wherein the forming the plurality of protrusions on the tube comprises removing material along a length of a longer tube and then slicing a length from the longer tube.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1:
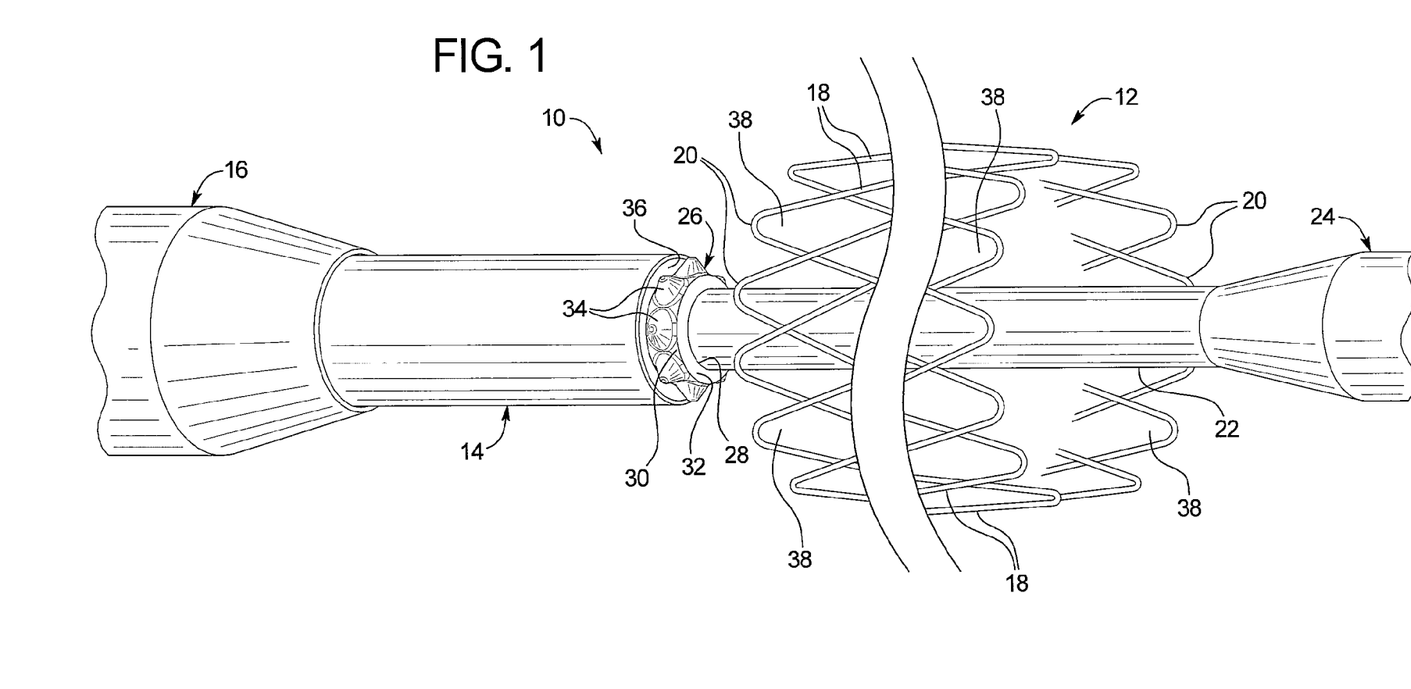
FIG. 1 is a side perspective view of a medical device, showing a self-expanding stent in an expanded state and an outer sheath withdrawn from the stent.

Referring now to the figures, and particularly to FIG. 1, a medical device 10 is shown. The medical device 10 may be used to deploy a self-expanding medical implant 12, such as a stent 12, using minimally invasive medical procedures. In FIG. 1, the self-expanding stent 12 is shown in the expanded state that the stent 12 would spontaneously expand to after being released from the inner catheter 14 and the outer sheath 16. Preferably, the stent 12 is a woven stent 12 made from one or more elastic wires 18, such as stainless steel or nitinol. Thus, the wires 18 pass over and under adjacent wires 18 that extend in opposite directions. At the ends of the stent 12, the wire(s) 18 are bent 20 and extend back into the body of the stent 12. However, the medical device 10 may also be used with other self-expanding medical implants 12, such as filters, valves, etc.

The outer sheath 16 is shown in the retracted position where it is not covering the stent 12 to permit the stent 12 to expand away from the inner catheter 14. Typically, the inner catheter 14 is provided with an outer diameter 22 upon which the stent 12 is mounted and compressed prior to deployment. The outer diameter 22 upon which the stent 12 is mounted is preferably located at the distal portion of the inner catheter 14. A distal tip 24 may also be provided at the distal end of the inner catheter 14 to provide an atraumatic tip to enable the medical device 10 to be more easily passed through a patient's body. As shown, the outer diameter 22 of the stent mounting region 22 is preferably smaller than the diameter of the distal tip 24.

A restraint member 26 may also be provided on the outer diameter 22 of the inner catheter 14 at the proximal end of the stent 12. The restraint member 26 is preferably a separate component from the inner catheter 14 that is bonded to the inner catheter 14. By making the restraint member 26 a separate component, the design of the medical device 10 offers a number of manufacturing advantages. Although the material of the restraint member 26 may be different from the material of the inner catheter 14, the materials of the restraint member 26 and the inner catheter 14 may also be the same. Preferably, the restraint member 26 is made from a polymer, such as nylon, PEEK, ABS, Delrin, or polyoxymethylene acetal but may also be made from metals. The restraint member 26 has an inner diameter 28 which is the portion of the restraint member 26 that is bonded to the inner catheter 14. The inner diameter 28 may be bonded to the outer diameter 22 of the inner catheter 14 upon which the stent 12 is mounted, or the restraint member 26 can be bonded to an increased diameter portion of the inner catheter 14. In any event, the outer diameter 22 of the inner catheter 14 upon which the stent 12 is mounted is smaller than the outer surface 30 of the restraint member 26. The restraint member 26 has a hub 32 that forms a thickness between the inner diameter 28 and the outer surface 30 of the hub 32. A series of protrusions 34 extend outward from the outer surface 30 of the hub 32. Essentially, the outer surface 30 of the hub 32 is a recessed region distinct from the protrusions 34 that extend out from the restraint member 26. The restraint member 26 may be bonded to the inner catheter 14 using adhesives, welding and other conventional techniques. The restraint member 26 may be bonded to the inner catheter 14 adjacent to a proximal stop surface 36 that extends outward to at least the outermost dimension of the restraint member 26. The stop surface 36 may be an integral portion of the inner catheter 14 with an increased diameter or may be a component that is bonded to the inner catheter 14. The stop surface 36 may also be an integral portion of the restraint member 26.

Figure 2:
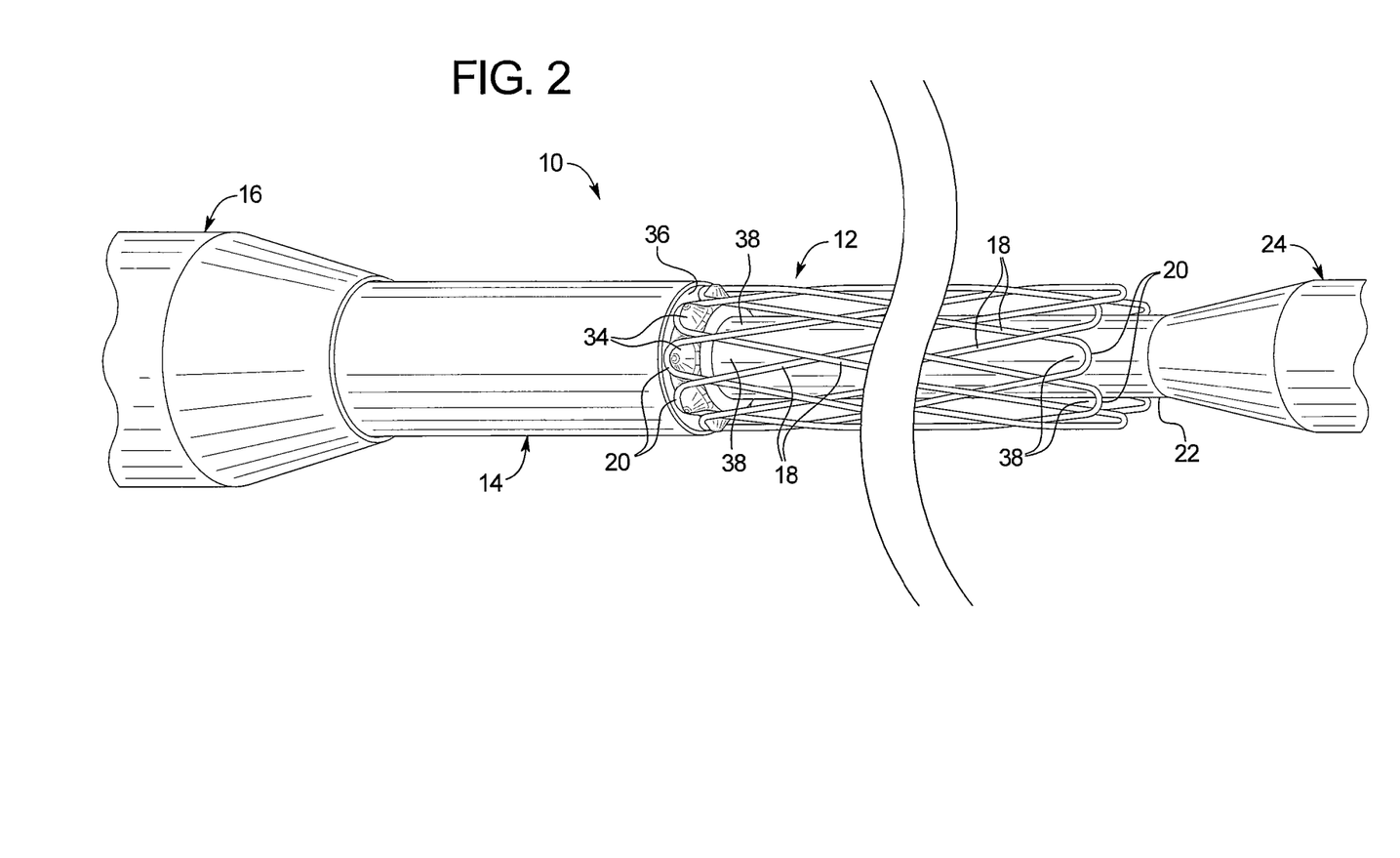
FIG. 2 is a side perspective view of the medical device, showing the stent compressed onto an inner catheter and a restraint member with the outer sheath withdrawn from the stent.

As shown in FIG. 2, the stent 12 may be compressed onto the inner catheter 14 so that the stent 12 provides a low profile for delivery through a patient's body. In this configuration, the protrusions 34 extend through the openings 38 in the stent 12 defined by the bends 20 at the proximal end of the stent 12. Preferably, no other protrusions on the restraint member 26 extends through the openings in the stent 12. Thus, the protrusions 34 that extend through the openings 38 in the bends 20 of the stent 12 form a row of protrusions around the circumference of the restraint member 26. The remaining portion of the stent 12, including the middle portion, extending distally from the bends 20 may be mounted directly on the outer diameter 22 of the inner catheter 14. Thus, distally from the bends 20 there may be an open space defined by the restraint member 26 at the proximal bends 20 of the stent 12 and between the stent 12 and the outer diameter 22 of the inner catheter 14. Within this open space, no other structures are positioned between the stent 12 and the outer diameter 22 of the inner catheter 14. Preferably, no portion of the outer diameter 22 of the inner catheter 14 within this region extends outward from the outer surface 30 of the restraint member 26. Even more preferably, no portion of the outer diameter 22 of the inner catheter 14 within this region extends outward from the inner diameter of the restraint member 26.

Figure 3:
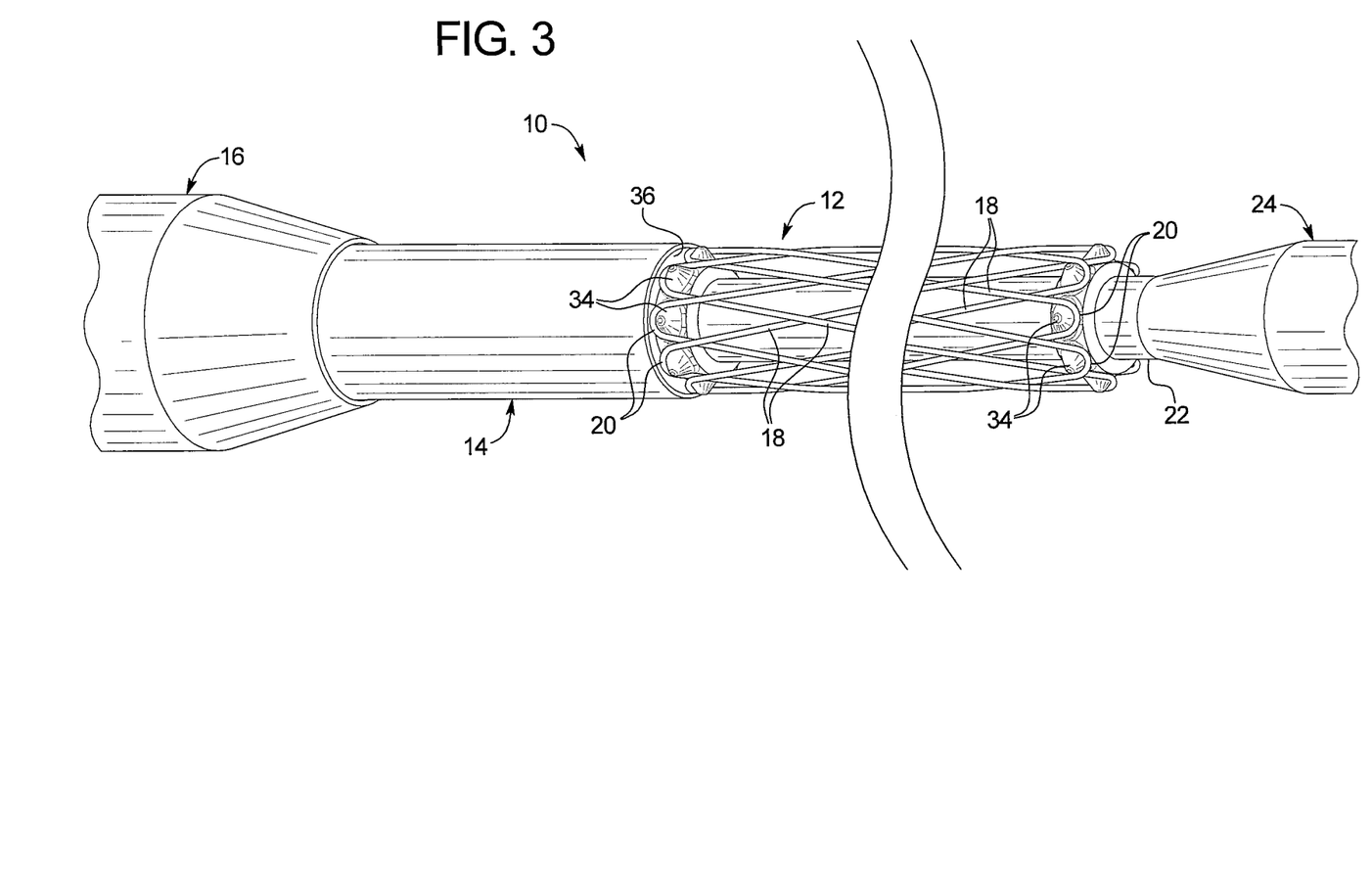
FIG. 3 is a side perspective view of the medical device, showing the stent compressed onto the inner catheter and one restraint member at the proximal end of the stent and another restraint member at the distal end of the stent with the outer sheath withdrawn from the stent.

As shown in FIG. 3, the medical device 10 may also be provided with a second restraint member 26 at the distal end of the stent 12. Like the restraint member 26 described above, the protrusions 34 of the second restraint member 26 extends through the openings 38 defined by the bends 20 in the stent wire(s) 18 at the distal end of the stent 12. Likewise, no other protrusions of the second restraint member 26 extends through the openings 38 in the stent 12. Thus, in this configuration, the open space is defined by the restraint member 26 at the proximal bends 20 in the stent 12 and the second restraint member 26 at the distal bends 20 in the stent 12.

Figure 4:
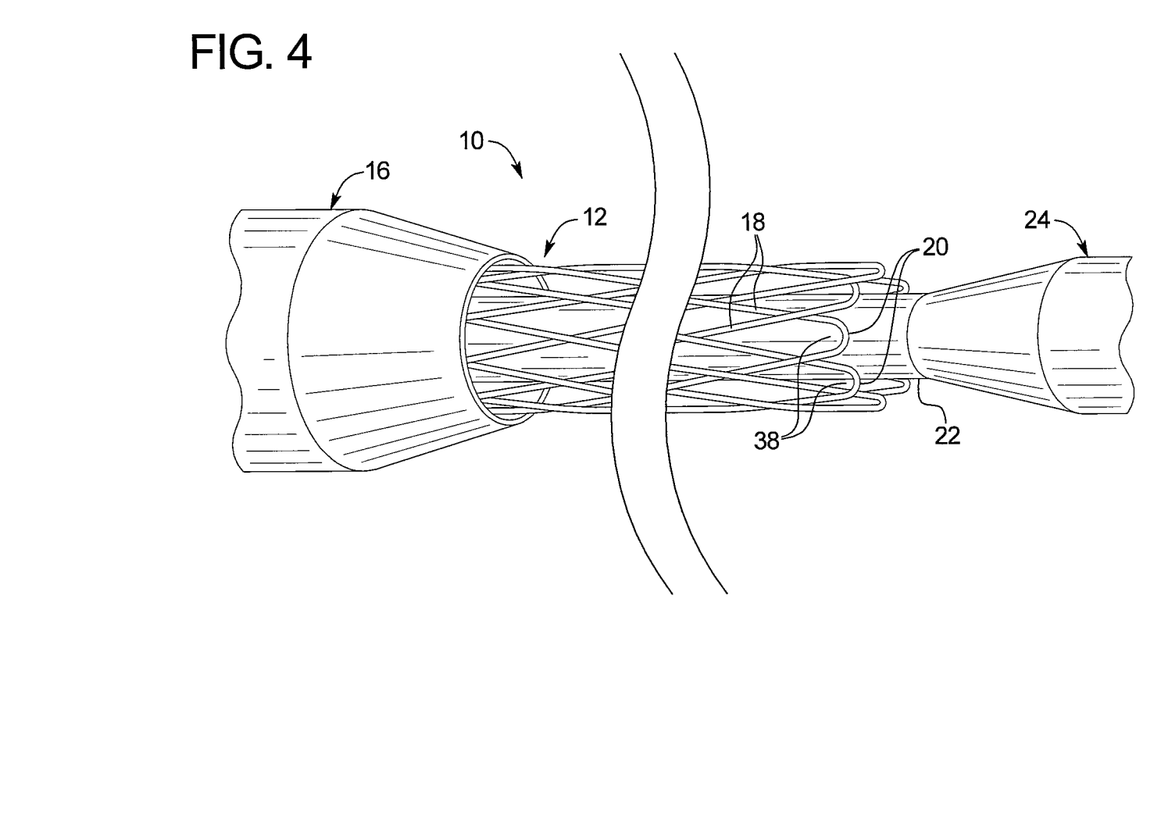
FIG. 4 is a side perspective view of the medical device, showing the stent compressed onto the inner catheter with the outer sheath disposed over the restraint member and partially over the stent.

As shown in FIG. 4, the outer sheath 16 covers the stent 12, inner catheter 14 and the restraint member 26 prior to deployment. For illustration, the outer sheath 16 is shown only covering part of the stent 12. However, prior to insertion into a patient's body and when moving the medical device 10 through the patient's body to the treatment site, the outer sheath 16 preferably fully covers the stent 12. Thus, in this configuration, the stent 12 presses outward against the outer sheath 16, but the outer sheath 16 prevents the stent 12 from self-expanding to its expanded state.

Figure 5A:
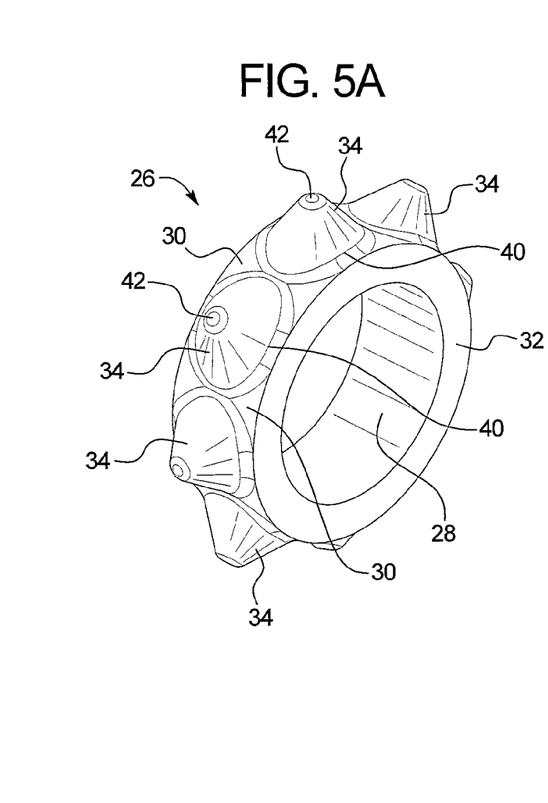
FIG. 5A is a perspective view of the restraint member with cone-shaped protrusions.
Figure 5B:
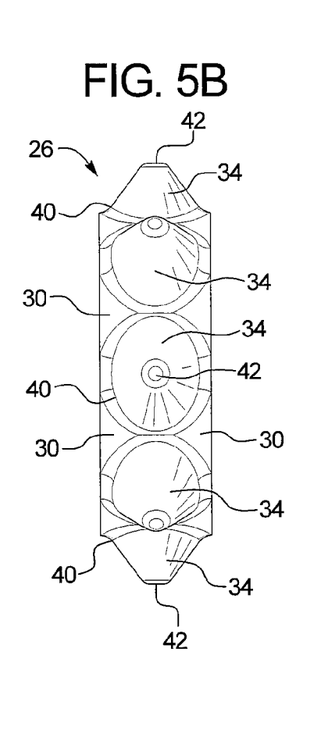
FIG. 5B is a side view of the restraint member with cone-shaped protrusions.
Figure 5C:
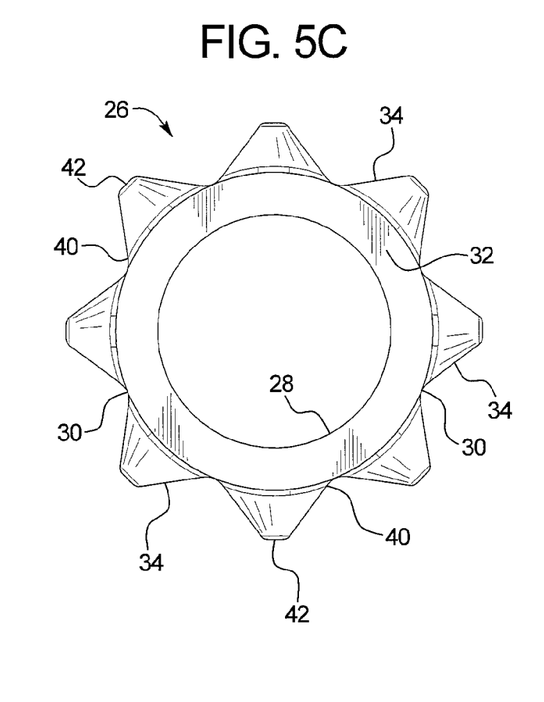
FIG. 5C is an end view of the restraint member with cone-shaped protrusions.

As shown in FIGS. 5A-5C, the restraint member 26 may have protrusions 34 that are cone-shaped. Each of the protrusions 34 have a base 40 at the outer surface 30 and an outer end 42 that extends away from the base 40. The base 40 of each protrusion 34 is larger than the outer end 42, and preferably, the surface of each protrusion 34 between the base 40 and outer end 42 has a constant linear narrowing shape. Thus, the protrusions 34 have inclined surfaces, which may be self-aligning with the stent 12 and may provide for less shearing and jamming compared to conventional delivery systems. Preferably, the inclined surfaces between the base 40 and outer end 42 are tapered more than 1° and less than about 30°, or more preferably, about 10° to about 20°. This particular taper may be desirable to allow a smoother release of the medical implant 12 while providing sufficient retention of the implant 12 during use. The particular taper chosen may also be useful during forming of the restraint member 26, particularly where a molding process is used. Although various manufacturing processes may be used to make the restraint member 26, the cone-shaped protrusions 34 are preferably made by building up the protrusions 34 in an additive manufacturing process. For example, some additive manufacturing processes include stereolithography, fused deposition modeling, etc. The protrusions 34 may be separately built up onto a separate hub 32, or the hub 32 and the protrusions 34 may be built up together by the same manufacturing process.

Figure 6A:
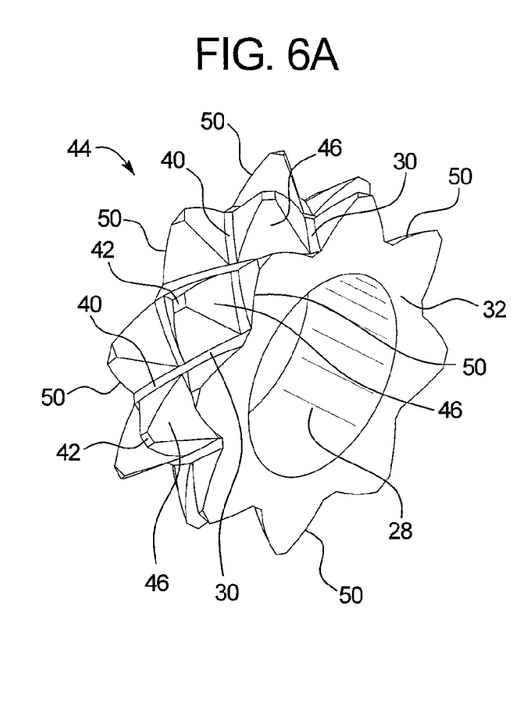
FIG. 6A is a perspective view of another restraint member with pyramid-shaped protrusions.
Figure 6B:
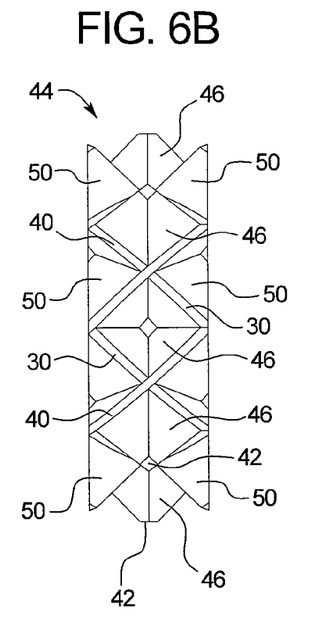
FIG. 6B is a side view of the restraint member with pyramid-shaped protrusions.
Figure 6C:
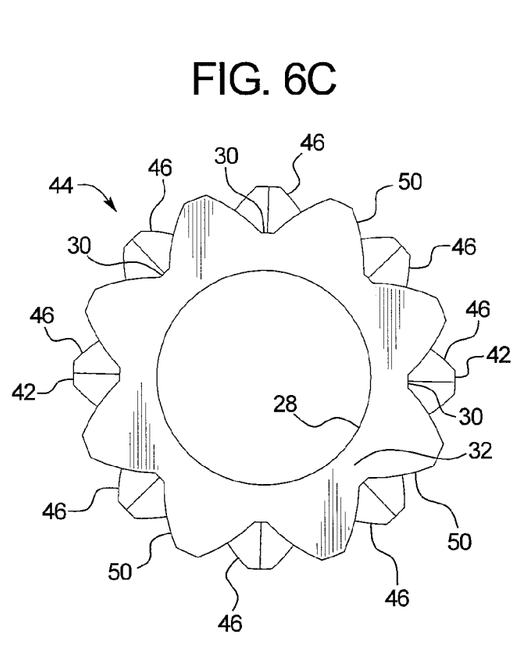
FIG. 6C is an end view of the restraint member with pyramid-shaped protrusions.
Figure 7:
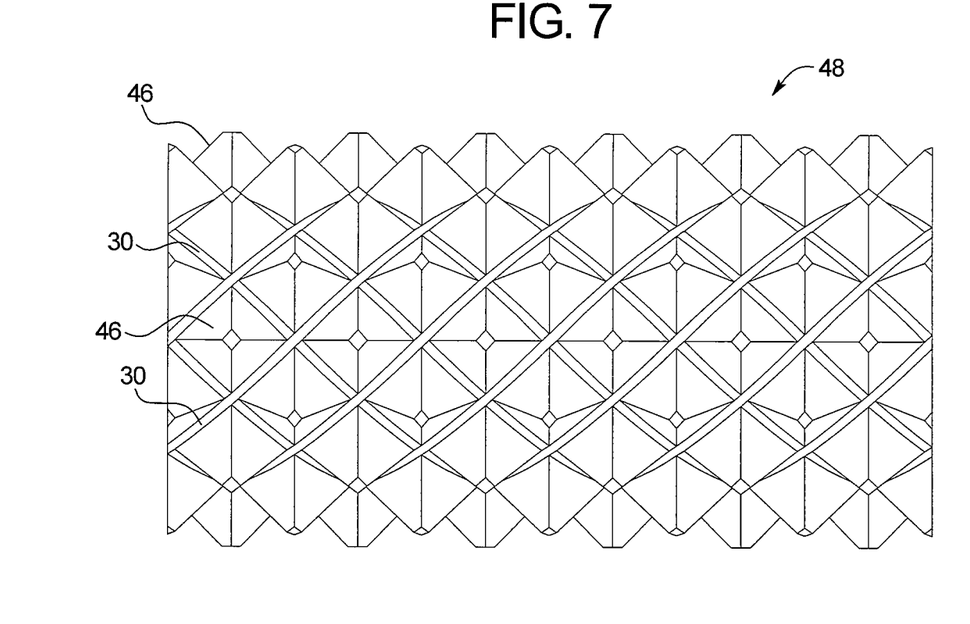
FIG. 7 is a side view of a longer tube that may be used to make the restraint member.
Figure 8:
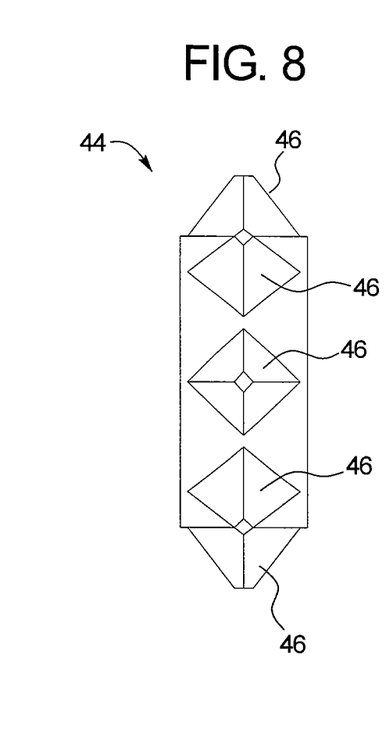
FIG. 8 is a side view of the restraint member with pyramid-shaped protrusions with the partial protrusions removed.

As shown in FIGS. 6A-6C, the restraint member 44 may also have protrusions 46 that are pyramid-shaped. Unlike the cone-shaped protrusions 34, the restraint member 44 with pyramid-shaped protrusions 46 is preferably made by removing material from the outer diameter of a tube. For example, as shown in FIG. 7, a long tube 48 may be machined with a mill to remove material in criss-crossing helixes to form the pyramid-shaped protrusions 46. The long tube 48 may then be sliced into shorter sections to form multiple restraint members 44. In the particular embodiment shown in FIGS. 6A-6C and 7, partial protrusions 50 are left on the restraint member 44 between the pyramid-shaped protrusions 46. However, the partial protrusions 50 preferably do not extend through any openings in the stent 12 and may not significantly interfere with the stent 12 in its compressed state. Alternatively, if the partial protrusions 50 extend through the openings 38 formed by the bends 20 of the stent 12, the partial protrusions 50 may be considered to be a part of the primary pyramid-shaped protrusions 46 extending through the same bend opening 38. As shown in FIG. 8, the partial protrusions 50 may also be removed if desired. This may be accomplished by milling horizontally across the long tube 48 or by milling circumferentially around the long tube 48.

Figure 9:
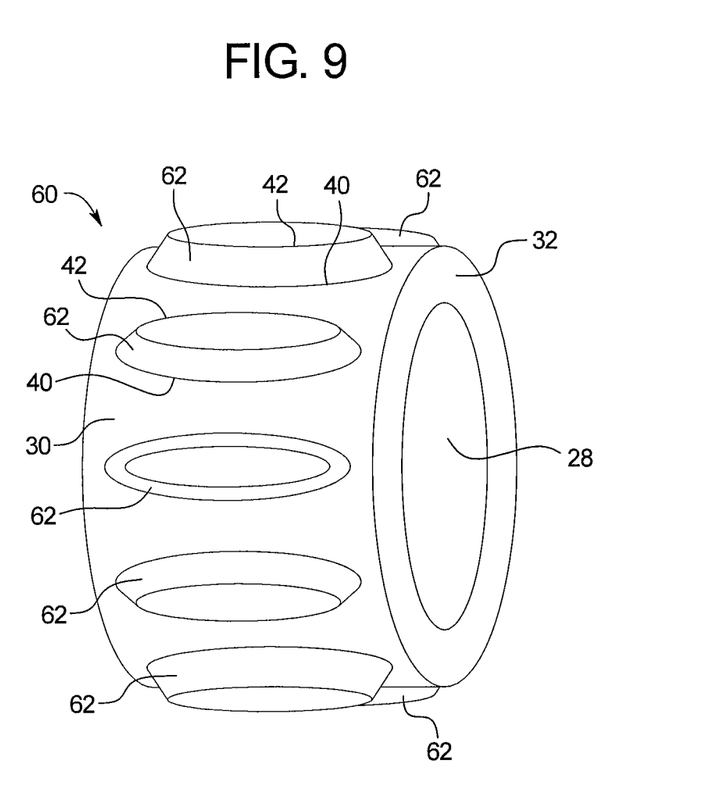
FIG. 9 is a perspective view of another restraint member with oblong-shaped protrusions.

As shown in FIG. 9, the restraint member 60 may also have protrusions 62 that are oblong-shaped with a length that is longer than the width of the protrusions 62. This may be useful to provide the protrusions 62 with improved longitudinal strength to resist stresses applied to the protrusions 62 by the medical implant 12 during use. For example, where the open area of each opening 38 (shown in FIG. 2) at the end of the stent 12 is defined by a terminal bend 20 and adjacent struts of the stent 12 when the stent 12 is compressed, the protrusions 62 may fill about 80% to about 90% of the open area of a respective opening 38. While any type of shaped protrusions may be sized to satisfy the desired fill ratio, the oblong-shaped protrusions 62 may be particularly suitable, especially where the medical implant 12 is a self-expanding woven stent 12.

The manufacturing process for the medical device 10 will typically be somewhat different from conventional manufacturing processes for self-expanding implant delivery devices. A preferred method for manufacturing the medical device 10 begins by attaining the inner catheter 14 by extrusion or other known methods. Preferably, the inner catheter 14 initially has an outer diameter 22 at the distal portion of the inner catheter 14 that extends all the way to the distal end and is sized for mounting the stent 12. In other words, there is no distal tip initially to increase the diameter of the inner catheter 14 at the distal end. The restraint member 26, 44, 60, or tube, is then slid over the distal end of the inner catheter 14 and along the outer diameter 22 of the inner catheter 14 to the location where the proximal end of the stent 12 will be mounted. The restraint member 26, 44, 60 may then be bonded to the inner catheter 14. As shown in FIG. 1, if a stop surface 36 is also provided, the restraint member 26, 44, 60 may be bonded so that the restraint member 26, 44, 60 abuts the stop surface 36. If a second restraint member 26, 44, 60 is desired, the second restraint member 26, 44, 60, or tube, can be slid over the distal end of the inner catheter 14 and along the outer diameter 22 of the inner catheter 14 after the first restraint member 26, 44, 60. The second restraint member 26, 44, 60 may then be bonded to the inner catheter 14. After the restraint members 26, 44, 60 are installed onto the inner catheter 14, the distal tip 24 may be bonded onto the distal end of the inner catheter 14. An expanded stent 12 may then be slid over the inner catheter 14 and positioned along the outer diameter 22 of the inner catheter 14 where the stent 12 will be mounted. As shown in FIGS. 2 and 3, the stent 12 may then be compressed onto the inner catheter 14 so that the protrusions 34, 46, 62 extend through the bend openings 38. As shown in FIG. 4, the outer sheath 16 may then be advanced over the compressed stent 12 until the outer sheath 16 fully covers the length of the stent 12 and covers the inner catheter 14 and restraint numbers 26, 44, 60.

One advantage of the manufacturing process is that protrusions 34, 46, 62 may be manufactured on the hub 32 of the restraint member 26, 44, 60 separately from the manufacturing processes used to make the inner catheter 14. The restraint member 26, 44, 60 may also be slid onto the outer diameter 22 of the inner catheter 14 and bonded to the inner catheter 14 in a relatively simple manner. However, this process requires the stent 12 to be compressed directly onto the inner catheter 14 and the restraint member 26, 44, 60. By contrast, many conventional manufacturing methods for self-expanding delivery systems involve compressing the stent separately by itself and then sliding the compressed stent into the outer sheath.

Another advantage of the medical device 10 is that it is particularly useful for self-expanding woven medical implants 12 like the stent 12 described above. One problem with woven stents 12 is that they tend to bunch in the middle of the stent 12 so that the diameter of the stent 12 is larger along the middle portion of the stent 12. However, with minimally invasive medical devices, it is desirable to minimize the overall diameter of the device as much as possible. With restraint systems that extend the length of the stent, the overall diameter of a delivery system for a woven stent 12 would be increased. However, in the preferred medical device 10 described herein, the middle portion of the stent 12 may be directly mounted on the outer diameter 22 of the inner catheter 14. Because the restraint member 26, 44, 60 is made as a separate component with a hub 32 that is slid onto the inner catheter 14, the outer surface 30 of the restraint member 26, 44, 60 is larger in diameter than the outer diameter 22 of the inner catheter 14. In many delivery systems, this feature would be a disadvantage because it would increase the overall diameter of the medical device. However, woven stents 12 tend to be more flexible at the ends and the bends 20 can be pressed outward slightly without increasing the overall diameter of the compressed stent 12 since the middle portion of the stent 12 is more determinative of the overall diameter of the compressed stent 12. Thus, in the medical device 10 described, the thicker middle portion of the stent 12 is mounted directly onto the inner catheter 14 to minimize the overall diameter of the stent 12, while the restraint member(s) 26, 44, 60 are positioned only under one or more ends of the stent 12 which has less effect on the overall diameter of the stent 12.

The restraint member 26, 44, 60 is especially useful to provide a solid connection between the stent 12 and the inner catheter 14. This is advantageous because the restraint member 26, 44, 60 can prevent the stent 12 from spontaneously being pulled out of the outer sheath 16 by the expansion of the distal end of the stent 12 when the outer sheath 16 is partially withdrawn. However, once the outer sheath 16 is fully withdrawn from the stent 12, the stent 12 freely expands outward away from the restraint member 26, 44, 60. The restraint member 26, 44, 60 may also permit the stent 12 to be resheathed after being partly deployed. For example, if the outer sheath 16 is partially withdrawn, but the outer sheath 16 is still covering the proximal end of the stent 12, the restraint member 26, 44, 60 can prevent the stent 12 for moving distantly relative to the inner catheter 14. Thus, the outer sheath 16 may be pushed distally to recompress the stent 12 without the stent 12 being pushed distally along the inner catheter 14. If a second restraint member 26, 44, 60 is used at the distal end of the stent 12, the second restraint member 26, 44, 60 may also be useful to resist proximal movement of the stent 12 relative to the inner catheter 14 that may occur as the outer sheath 16 is initially withdrawn due to friction between the stent 12 and the outer sheath 16. The restraint member(s) 26, 44, 60 may also be made from radiopaque material to enable the physician to more accurately identify the location of the medical device 10.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

I claim:

1. A medical device, comprising:
    an inner catheter comprising an outer diameter along a distal portion of said inner catheter;
    a restraint member disposed on said inner catheter, said restraint member comprising an inner diameter, a hub extending from said inner diameter and around said restraint member, and a plurality of protrusions extending outward from an outer surface of said hub, each of said protrusions comprising a base at said outer surface of said hub and an outer end, said base being larger than said outer end, wherein said restraint member comprises a row of said protrusions around a circumference of said hub, said inner diameter of said restraint member being bonded to said inner catheter along said distal portion of said inner catheter;
    a self-expanding stent compressed onto said inner catheter and said restraint member, said self-expanding stent comprising elastic wire with a plurality of bends at a proximal end and a distal end of said stent, said wire being woven between said proximal and distal ends, wherein each of said protrusions extends through an opening formed by one of said bends at said proximal end of said stent, said hub thereby being disposed under said proximal end of said stent and no other protrusions on said restraint member extending through an opening of said stent, a middle portion of said stent being disposed on said outer diameter of said inner catheter, wherein said outer diameter of said inner catheter is smaller than said outer surface of said hub of said restraint member;
    an outer sheath disposed over said inner catheter, said restraint member, and said stent; and
    wherein said restraint member comprises a row of partial protrusions around the circumference of said hub offset from said row of protrusions so that the partial protrusions do not extend through any openings in said self-expanding stent.

2. The medical device according to claim 1, wherein said protrusions are oblong-shaped.

3. The medical device according to claim 2, wherein said protrusions fill about 80% to about 90% of the open area of each of said openings, said open areas being defined by said bends and adjacent struts of said stent when said stent is compressed.

4. The medical device according to claim 1, wherein said protrusions are tapered from said base to said outer end about 10° to about 20°.

5. The medical device according to claim 1, wherein said protrusions are cone-shaped.

6. The medical device according to claim 1, wherein said protrusions are pyramid-shaped.

7. The medical device according to claim 1, wherein said restraint member is made from a polymer.

8. The medical device according to claim 1, further comprising a stop surface disposed proximally adjacent said hub of said restraint member, said stop surface extending outward from said outer surface of said hub.

9. The medical device according to claim 1, further comprising a second restraint member disposed at said distal end of said stent, wherein each of said protrusions of said second restraint member extends through an opening formed by one of said bends at said distal end of said stent, said hub of said second restraint member thereby being disposed under said distal end of said stent and no other protrusions on said second restraint member extending through an opening of said stent.

10. The medical device according to claim 1, wherein an open space is disposed between said bends of said proximal end and said distal end of said stent and said stent and said outer diameter of said inner catheter, no portion of said outer diameter of said inner catheter extending outward from said outer surface of said restraint member between said bends of said proximal end and said distal end of said stent.

11. The medical device according to claim 1, wherein an open space is disposed between said bends of said proximal end and said distal end of said stent and said stent and said outer diameter of said inner catheter, no portion of said outer diameter of said inner catheter extending outward from said inner diameter of said restraint member between said bends of said proximal end and said distal end of said stent.

12. The medical device according to claim 1, wherein said restraint member is made from a polymer, further comprising a stop surface disposed proximally adjacent said hub of said restraint member, said stop surface extending outward from said outer surface of said hub, and wherein an open space is disposed between said bends of said proximal end and said distal end of said stent and said stent and said outer diameter of said inner catheter, no portion of said outer diameter of said inner catheter extending outward from said outer surface of said restraint member between said bends of said proximal end and said distal end of said stent.

13. The medical device according to claim 12, wherein no portion of said outer diameter of said inner catheter extends outward from said inner diameter of said restraint member between said bends of said proximal end and said distal end of said stent.

14. The medical device according to claim 13, further comprising a second restraint member disposed at said distal end of said stent, wherein each of said protrusions of said second restraint member extends through an opening formed by one of said bends at said distal end of said stent, said hub of said second restraint member thereby being disposed under said distal end of said stent and no other protrusions on said second restraint member extending through an opening of said stent.

15. The medical device according to claim 13, wherein said protrusions are oblong-shaped, said protrusions fill about 80% to about 90% of the open area of each of said openings, said open areas being defined by said bends and adjacent struts of said stent when said stent is compressed, and said protrusions are tapered from said base to said outer end about 10° to about 20°.

16. The medical device according to claim 1, further comprising a stop surface disposed proximally adjacent said hub of said restraint member, said stop surface extending outward from said outer surface of said hub, and wherein an open space is disposed between said bends of said proximal end and said distal end of said stent and said stent and said outer diameter of said inner catheter, no portion of said outer diameter of said inner catheter extending outward from said inner diameter of said restraint member between said bends of said proximal end and said distal end of said stent.

17. The medical device according to claim 16, wherein said protrusions are oblong-shaped.

18. The medical device according to claim 17, wherein said protrusions fill about 80% to about 90% of the open area of each of said openings, said open areas being defined by said bends and adjacent struts of said stent when said stent is compressed, and said protrusions are tapered from said base to said outer end about 10° to about 20°.

19. A method of manufacturing a medical device, comprising:
providing an inner catheter comprising an outer diameter along a distal portion of said inner catheter;
providing a tube comprising an inner diameter;
forming a plurality of protrusions on said tube, wherein after forming said protrusions said tube comprises an outer surface with said protrusions extending outward therefrom and a thickness between said inner diameter and said outer surface;
sliding said inner diameter of said tube over a distal end and said outer diameter of said inner catheter;
bonding said inner diameter of said tube to said inner catheter;
compressing a self-expanding stent onto said inner catheter and said tube, wherein said stent comprises elastic wire with a plurality of bends at a proximal end and a distal end of said stent, said wire being woven between said proximal and distal ends, wherein each of said protrusions extends through an opening formed by one of said bends at said proximal end of said stent, said tube thereby being disposed under said proximal end of said stent and no other protrusions on said tube extending through an opening of said stent, a middle portion of said stent being disposed on said outer diameter of said inner catheter, wherein said outer diameter of said inner catheter is smaller than said outer surface of said tube;
sliding an outer sheath over said compressed stent, said inner catheter and said tube; and
wherein said tube comprises a row of partial protrusions around the circumference of the outer surface of the tube offset from said protrusions so that the partial protrusions do not extend through any openings in said self-expanding stent.

20. The method according to claim 19, further comprising:
bonding a distal tip onto said distal end of said inner catheter after sliding said tube over said distal end and before said stent is compressed onto said inner catheter;
sliding an inner diameter of another of said tube over said distal end and said outer diameter of said inner catheter;
bonding said inner diameter of said another of said tube to said inner catheter;
wherein each of said protrusions of said another of said tube extends through an opening formed by one of said bends at said distal end of said stent, said another of said tube thereby being disposed under said distal end of said stent and no other protrusions on said another of said tube extending through an opening of said stent
said forming said plurality of protrusions on said tube comprises removing material from said tube; and
said forming said plurality of protrusions on said tube comprises removing material along a length of a longer tube and then slicing a length from said longer tube.

21. The medical device according to claim 6, wherein said protrusions are separated by a criss-crossing helix pattern on the outer surface of said hub.

22. The medical device according to claim 6, wherein said protrusions are four-sided pyramid-shaped.

* * * * *